US009626483B2

(12) United States Patent
Barrett et al.

(10) Patent No.: US 9,626,483 B2
(45) Date of Patent: Apr. 18, 2017

(54) MEDICATION ADMINISTERING APPARATUS

(71) Applicant: Advantage Pharmacy Services LLC, Madison, MS (US)

(72) Inventors: John Todd Barrett, Madison, MS (US); Fred P. Schoville, Brighton, MI (US)

(73) Assignee: Advantage Pharmacy Services LLC, Madison, MS (US)

( * ) Notice: Subject to any disclaimer, the term of this patent is extended or adjusted under 35 U.S.C. 154(b) by 559 days.

(21) Appl. No.: 13/910,556

(22) Filed: Jun. 5, 2013

(65) Prior Publication Data

US 2013/0331983 A1    Dec. 12, 2013

Related U.S. Application Data

(60) Provisional application No. 61/656,838, filed on Jun. 7, 2012.

(51) Int. Cl.
  *G06F 19/00*    (2011.01)
  *A61G 12/00*    (2006.01)
  *A61J 7/00*    (2006.01)

(52) U.S. Cl.
  CPC ....... *G06F 19/3462* (2013.01); *A61G 12/001* (2013.01); *A61J 7/0084* (2013.01)

(58) Field of Classification Search
  USPC .......................................... 700/236, 241, 242
  See application file for complete search history.

(56) References Cited

U.S. PATENT DOCUMENTS 6,011,999 A * 1/2000 Holmes ................... E05B 65/46
                                                         312/215
6,175,779 B1    1/2001 Barrett
(Continued)

FOREIGN PATENT DOCUMENTS

EP        2 270 759 A1   1/2011
WO   WO 2009/061095 A2   5/2009

OTHER PUBLICATIONS

Ramtron Internation Corporation, "Product Brief: WM72016", Copyright 2010, Revised Sep. 2011.*

*Primary Examiner* — Timothy Waggoner
*Assistant Examiner* — Stephen Akridge
(74) *Attorney, Agent, or Firm* — Reising Ethington, P.C.

(57) ABSTRACT

A method of administering medication. Medication is stored in a plurality of drawers wherein each of the plurality of drawers includes a drawer electrical connector, a medication conveyor, and a non-volatile read/write memory to store data about the drawer. A drawer of the plurality of drawers is inserted into a receptacle of a housing, wherein the receptacle is one of a plurality of receptacles, and the housing also includes a plurality of housing electrical connectors corresponding to the plurality of receptacles, wherein one of the housing electrical connectors is coupled to the electrical connector of the drawer when the drawer is inserted in the receptacle. Data is selectively transmitted from among non-volatile read/write memory of the plurality of drawers to a computer in communication with the plurality of housing electrical connectors, wherein when the drawer is inserted into the receptacle such that the drawer and housing electrical connectors are operatively engaged, the memory of the inserted drawer is triggered to transmit data stored therein to the computer.

18 Claims, 6 Drawing Sheets

(56) References Cited

U.S. PATENT DOCUMENTS

| | | |
|---|---|---|
| 6,935,560 B2 | 8/2005 | Andreasson et al. |
| 7,250,865 B2 | 7/2007 | Maloney |
| 7,440,818 B2 * | 10/2008 | Handfield ............. A61J 7/0084 |
| | | 221/4 |
| 7,910,993 B2 * | 3/2011 | Brindle ............. H01L 29/78609 |
| | | 257/347 |
| 2002/0173875 A1 * | 11/2002 | Wallace ................ G06F 19/322 |
| | | 700/242 |
| 2005/0049747 A1 * | 3/2005 | Willoughby .......... A61J 7/0084 |
| | | 700/232 |
| 2006/0125356 A1 | 6/2006 | Meek, Jr. et al. |
| 2009/0091453 A1 | 4/2009 | Ishida et al. |
| 2010/0114367 A1 * | 5/2010 | Barrett ................ G06F 19/3456 |
| | | 700/236 |
| 2012/0203377 A1 * | 8/2012 | Paydar ................... G01K 3/005 |
| | | 700/232 |

* cited by examiner

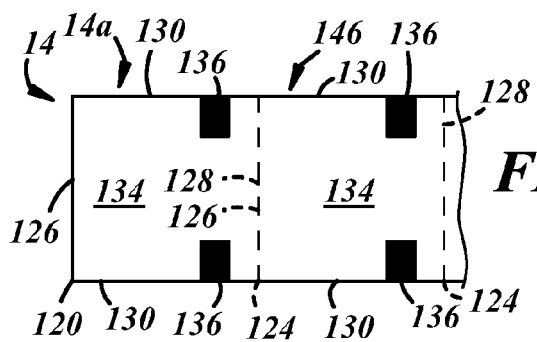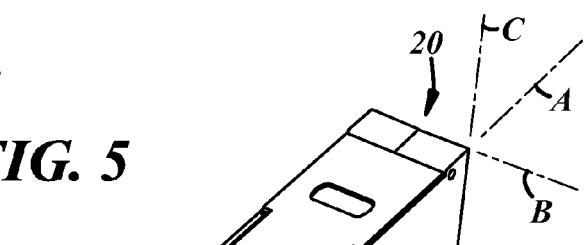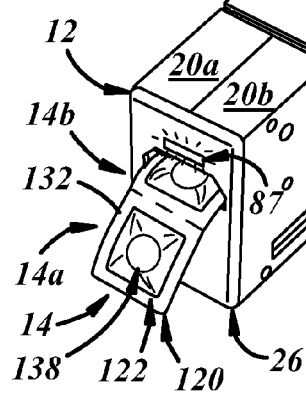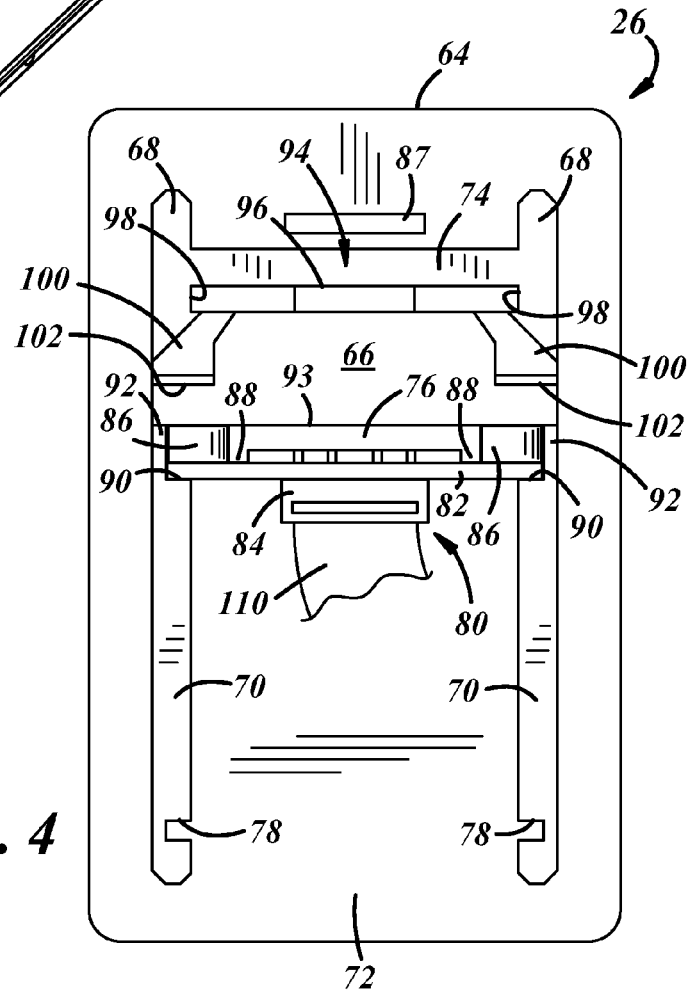

MEDICATION ADMINISTERING APPARATUS

TECHNICAL FIELD

The field to which the disclosure generally relates includes apparatuses and methods for administering medication.

BACKGROUND

Computerized medication cabinets may be stationary or mobile and are frequently used in medical care facilities to administer medication to patients on a patient-by-patient basis. For example, such cabinets may include a plurality of drawers to hold and release medication. The drawers may include memory that stores medication data, and the cabinet may include a computer to poll memory of each drawer and store the data in a computer database.

But such cabinets may require a minute or more to read the memory and/or may inadvertently confuse data read from memory of one drawer with data read from memory of another drawer. For example, with some cabinets, whenever a drawer is inserted into the cabinet or whenever medication is administered from a drawer, the cabinet computer polls the memory of all of the drawers in a chain-like manner to update the computer database. But although polling is supposed to proceed sequentially from drawer-to-drawer, oftentimes memory from two or more of the drawers are read out of order. Accordingly, data from one drawer becomes confused with data from another drawer in the computer database.

SUMMARY

A method of administering medication. Medication is stored in a plurality of drawers wherein each of the plurality of drawers includes a drawer electrical connector, a medication conveyor, and a non-volatile read/write memory to store data about the drawer. A drawer of the plurality of drawers is inserted into a receptacle of a housing, wherein the receptacle is one of a plurality of receptacles, and the housing also includes a plurality of housing electrical connectors corresponding to the plurality of receptacles, wherein one of the housing electrical connectors is coupled to the electrical connector of the drawer when the drawer is inserted in the receptacle. Data is selectively transmitted from among non-volatile read/write memory of the plurality of drawers to a computer in communication with the plurality of housing electrical connectors, wherein when the drawer is inserted into the receptacle such that the drawer and housing electrical connectors are operatively engaged, the memory of the inserted drawer is triggered to transmit data stored therein to the computer.

BRIEF DESCRIPTION OF THE DRAWINGS

Illustrative embodiments of the invention will become more fully understood from the detailed description and the accompanying drawings, wherein:

FIG. 2 is a perspective view of one of the drawers of FIG. 1;

FIG. 4 is a rear view of a front cover of the drawer of FIG. 3;

FIG. 5 is a bottom view of a medication packaging strip of FIG. 2;

DETAILED DESCRIPTION OF ILLUSTRATIVE EMBODIMENTS

The following description of the embodiment(s) is merely illustrative in nature and is in no way intended to limit the invention, its application, or uses.

Figure 1:
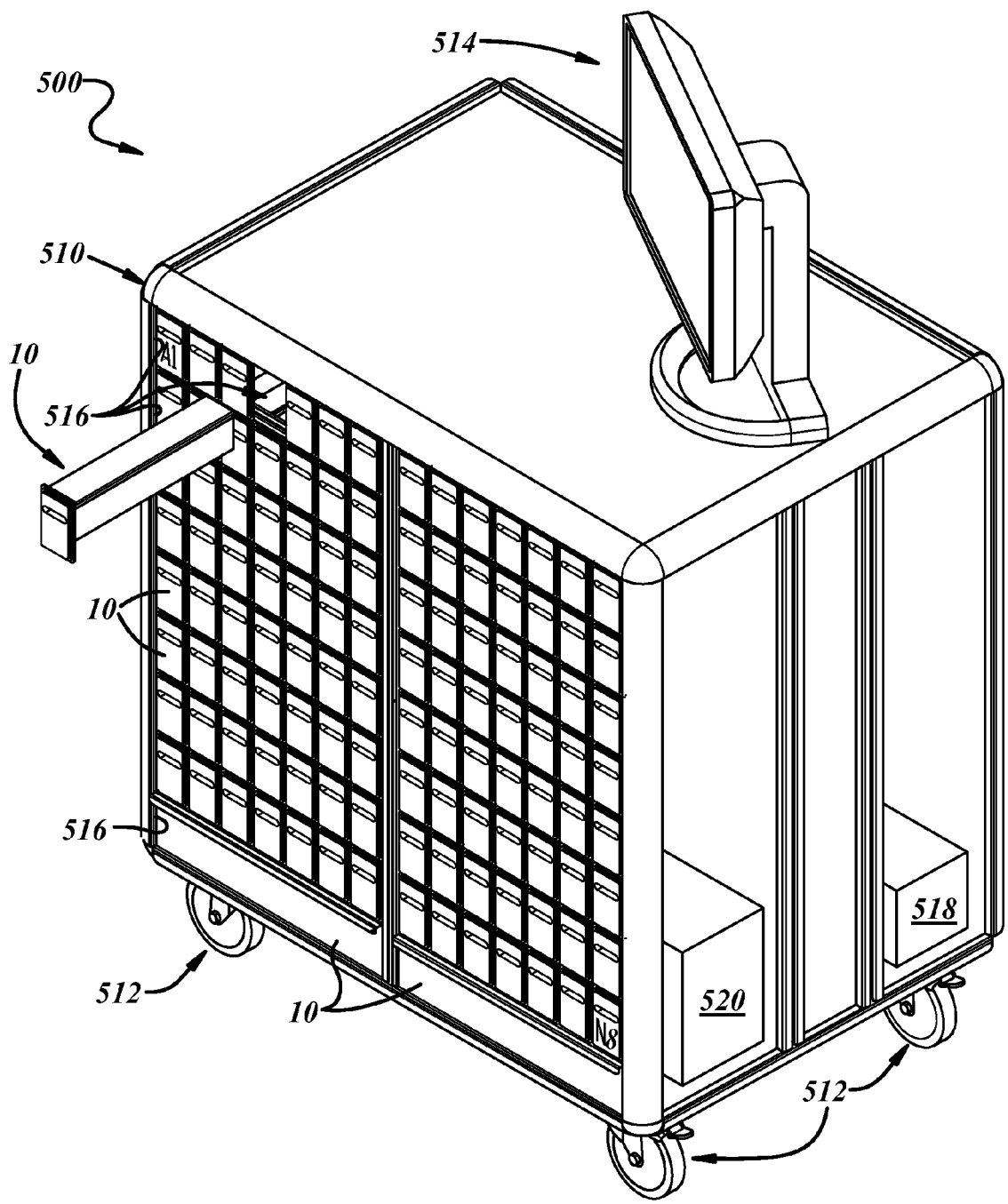
FIG. 1 is a perspective view of an illustrative embodiment of a medication administering apparatus including a housing having plurality of receptacles for a plurality of drawers for holding and releasing medication.

FIG. 1 illustrates an apparatus 500 including a cabinet or housing 510, a plurality of medication drawers 10, and a plurality of compartments or receptacles 516 corresponding to the drawers 10 for receiving the drawers 10. According to an example embodiment, the housing 510 may include a mobile, computerized, medication administering cart or wheeled cabinet, as shown. For example, a plurality of wheels 512 may be mounted to the apparatus 500 to permit transport of the apparatus 500 from room to room by a medication administering attendant while making patient rounds. In another embodiment, the apparatus 500 may be stationary, for example, built into a workstation, desk, or the like in any suitable facility. Also, the apparatus 500 may include a user interface 514 carried by the apparatus 500 for easy access and view by the attendant. The interface 514 may include a touch screen monitor, or may include a conventional monitor and a mouse and/or keyboard, or any other suitable configuration to receive and display information.

The drawers 10 may be used to store medication, bandages and other types of medical supplies as well as other medications that cannot be easily packaged such as medications in liquid form, creams, lotions, powders, etc. for administering to a patient. For security purposes, such drawers 10 may be locked or latched. As used herein, the term "drawer" includes any suitable device, component, cassette, or the like that may be slid into and out of another apparatus, for example, a cabinet, cart, or the like. The terminology drawer and cassette are used interchangeably herein.

The apparatus 500 also may include a computer 520 and one or more power supplies 518 for powering the computer 520, powerable portions of the drawers 10, powerable drawer release and/or ejection mechanisms of the housing 510, and any other powerable elements of the apparatus 500. Of course, the apparatus 500 may be supplied with power in any suitable manner, including DC battery power, AC utility power, or AC generator power, and/or the like, and including any suitable transformers, conditioners, and/or the like. The computer 520 may include memory, one or more processors coupled to the memory, and any suitable interfaces coupled to the processor(s) for coupling the computer 520 to any suitable input and output devices. Also, the computer 520 may be an electronic medication administration record (emar) computer and may or may not include hardware other than the memory, processors, and interfaces. Further, the computer 520 may include a single computer or may include multiple separate computers that cooperate.

FIG. 2 illustrates the medication cassette or drawer 10. The drawer 10 may include a longitudinal axis A, a horizontal axis B, and a vertical axis C. The illustrative drawer 10 includes a housing 12 to house a medication packaging strip 14 and provide support for other components of the drawer 10.

Figure 3:
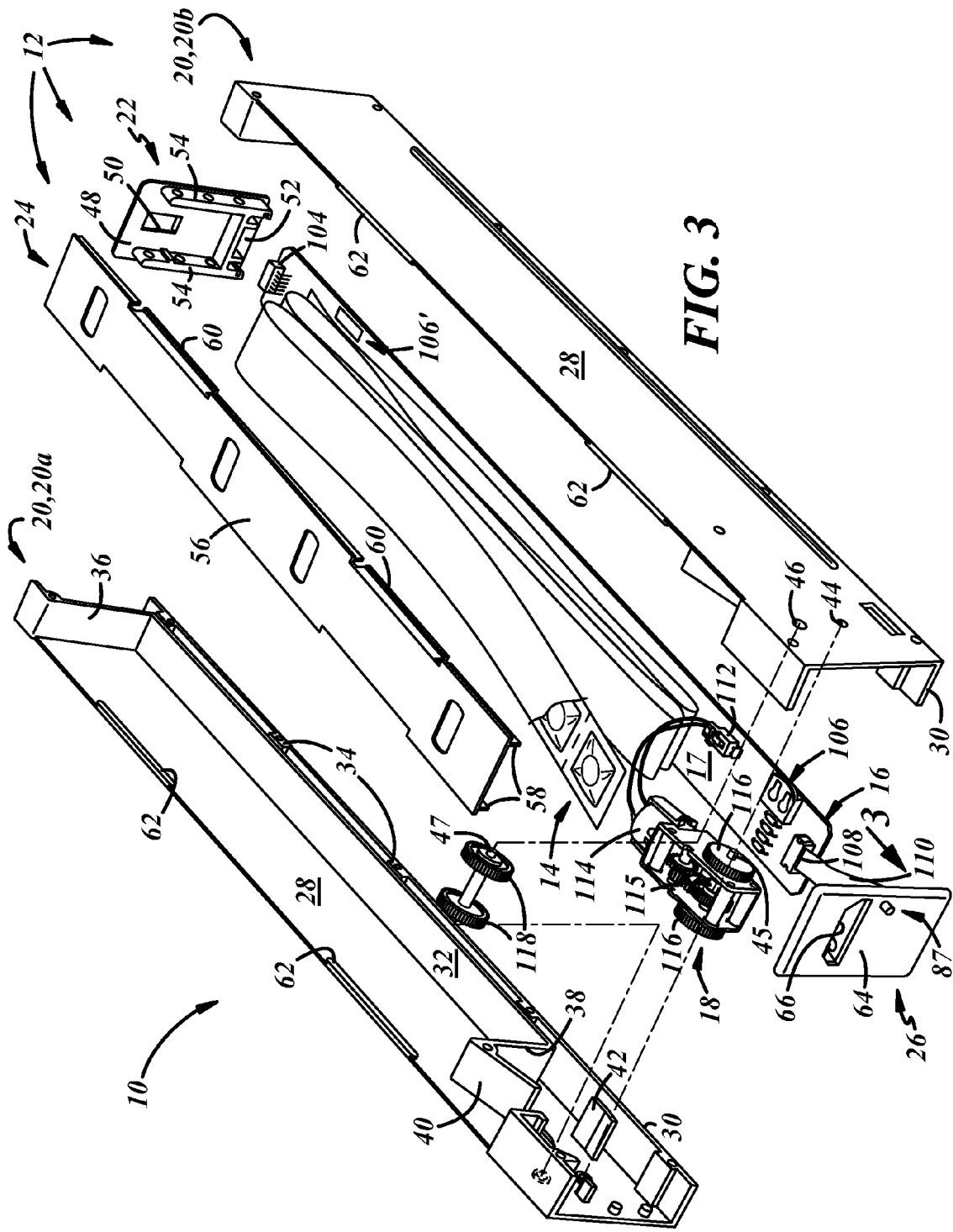
FIG. 3 is an exploded perspective view of the drawer of FIG. 2.

For example, as illustrated in FIG. 3, the housing 12 also may house a circuit board assembly 16 including a circuit board 17, and a medication conveyor or material handler 18 of the drawer 10. The housing 12 may include a main body 20 that may be unitary or that may include multiple portions, for example, left and right sides 20a, 20b that may be mirror images of one another and may be fastened, clipped, snap-fit, adhered, and/or coupled together in any other suitable manner. The housing 12 also may include a rear cover 22 that may rearwardly cover the main body 20, a top cover 24 that may cover an upper portion of the main body 20, and a front cover 26 that may frontally cover the main body 20. The housing 12 may be produced in any suitable manner, for example, casting, molding, machining, or the like.

The main body 20 may include sidewalls 28, a bottom wall 30 that may extend between the sidewalls 28, and a bottom compartment wall 32 that may extend between the sidewalls 28 vertically spaced from the bottom wall 30. The main body 20 also may include projections 34 that may extend from the bottom wall 30 toward the bottom compartment wall 32 for retaining the circuit board assembly 16 therebetween, rear and front compartment walls 36, 38 that may extend upwardly from the bottom compartment wall 32 and between the sidewalls 28, and a packaging strip guide wall 40 that may extend between the sidewalls 28 and forwardly from the front compartment wall 38. The main body 20 also may include a material handler support wall 42 that may extend between the sidewalls 28 and may be located between a forward portion of the guide wall 40 and a forward end of the main body 20. The sidewalls 28 also may include apertures 44, 46 to accept shafts 45, 47 of the material handler 18.

The rear cover 22 may include a base wall 48 that may have a locking latch aperture 50 and an electrical connector passage 52 therethrough. The rear cover 22 also may include flanges 54 extending from the base wall 48 for coupling to the main body 20 of the housing 12. The rear cover 24 may be may be fastened, clipped, snap-fit, adhered, and/or coupled to the main body 20 in any other suitable manner.

The top cover 24 may include a base wall 56, with flanges 58 and engagement features 60 extending therefrom. The top cover 24 may be coupled to the main body 20 in any suitable manner. For example, the top cover 24 may be clipped to the main body 20 using the engagement features 60 that may engaged corresponding engagement features 62 of the main body 20. The engagement features 62 may be corresponding lips or projections constructed and arranged for interference fit with one another, and may include cooperating geometries suitable for tamper-resistant locking to one another.

As best shown in FIG. 4, the front cover 26 may include a base wall 64 with a packaging strip outlet 66 therethrough, and upper and lower vertical flanges 68, 70 extending from a rear surface 72 of the base wall 64 that may be used for coupling to the main body 20. The front cover 26 also may include an upper horizontal flange 74 extending from the rear surface 72 between the upper vertical flanges 68, a lower horizontal flange 76 across the outlet 66 from the upper horizontal flange 74 and extending from the rear surface 72 between the lower vertical flanges 70. The lower vertical flanges 70 may define a slot 78 to receive a front portion of the circuit board assembly 16.

Also, the front cover 26 may carry another circuit board assembly 80 that may include a circuit board 82, a connector 84 coupled to the circuit board 82, and one or more sensors 86 that may be carried by the circuit board 82 upstream of the outlet 66 and may be flush with an upper surface of the lower horizontal flange 76. The circuit board assembly 80 also may include a light 87 that may be electrically coupled to the circuit board 82 in any suitable manner and may extend through a corresponding aperture in the base wall 64 of the front cover 26. The sensors 86 may include one or more optical or reflective object sensors, for instance, each including a gallium arsenide infrared emitting diode and an NPN silicon phototransistor. The sensors 86 may include OPB710F sensors available from OPTEK of Carrollton, Tex. The light 87 may include one or more light emitting diodes (LEDs), an LED bar, or any other suitable lighting device(s).

The circuit board 82 may be mounted to the front cover 26, for example, by being positioned between portions of the lower vertical flanges 70 and the lower horizontal flange 76. More specifically, the circuit board 82 may be frictionally engaged by and vertically between legs 88 of the lower horizontal flange 76 and shoulders 90 of the lower vertical flanges 70. Also, the circuit board 82 may be frictionally engaged by and horizontally between extensions 92 of the lower vertical flanges 70. In any case, the sensors 86 may be positioned adjacent to the outlet 66 and operatively disposed in a vertical orientation to sense sensor pickups on a packaging strip to be released out of the outlet 66, for example, for administration to a patient by suitable medical personnel. For instance, upper surfaces of the sensors 86 may be flush with upper surfaces 93 of the front cover 26 at the opening 66 thereof.

Further, the front cover 26 may include a packaging strip restraint or guide 94. The guide 94 may be a separate component carried by the front cover 26 or may be integral with the front cover 26. The guide 94 may include a base wall 96 that may be carried in a corresponding slot 98 that may be defined by the upper vertical flanges 68 adjacent the upper horizontal flange 74. The guide 94 also may include legs 100 extending from the base wall 96. The legs 100 may extend outwardly at an angle, for example, about 45 degrees, for instance, 30 to 60 degrees. Accordingly, the legs 100 may extend outboard of the lateral extent of the base wall 96.

Referring to FIG. 3, the circuit board assembly 16 also may include an electrical connector 104 that may be coupled to the circuit board 17 in any suitable manner and that may at least partially pass through the connector passage 52 of the rear cover 22. The connector 104 may engage a corresponding electrical connector of the apparatus in which the drawer 10 is used. For example, the connector 104 may be configured for coupling to an electrical backplane (not shown) of such an apparatus. The circuit board assembly 16 also may include non-volatile memory 106 that may be disposed at a front end of the circuit board 17, a connector 108 and associated wires 110 coupled to the front end of the circuit board 17 and to the other circuit board assembly 80 carried by the front cover 26, and a motor wire connector 112 coupled to the circuit board 17 and to the material handler 18.

The memory 106 may include a non-volatile read/write memory that may be serialized with a unique identifier to distinguish memory from drawer to drawer. The memory 106 may include a wired memory, for instance, wire EEPROM memory, or any other suitable type of wired memory. For example, the memory 106 may include an iButton® brand device, for instance, a 4 kB, 16 bit model DS1973 available from Maxim of Sunnyvale, Calif. As used herein, the terminology "wired memory" means that the memory itself does not communicate via wireless communication.

Also, or instead, the circuit board assembly 16 may include a different non-volatile memory 106' which may include a wireless, radio frequency (RF) integrated circuit (RFIC) or RF identification (RFID) tag. For example, the memory 106' may include a RAMTRON brand RFIC memory, for instance, a 32 kB, 32 bit model WM72016 available from Ramtron of Colorado Springs, Colo. In another embodiment, the wired memory 106 may be excluded entirely.

The memory 106 and/or 106' may store data about the drawer 10, for instance, the medication carried by the drawer 10 and may include one or more of the following data fields: GCN code, medication manufacturer, lot number, expiration data, NDC code, drawer/memory serial number, medication count, and reorder/trip count. The memory 106 and/or 106' may be populated with data at a pharmacy, where the drawer 10 may be packed with the medication and thereafter sealed, in any suitable manner. The medication may be verified, counted, and loaded to the drawer by a pharmacist who also may enter the data about the drawer into a pharmacy computer, which as described below, can be networked to the apparatus computer 520. Any suitable apparatus may be used to communicate the drawer data to the memory 106, 106', like a docking station having a connector to couple to the drawer connector, or an RF interrogator, or the like. Thereafter, the drawer 10 can be shipped or delivered to the apparatus 500 and inserted in an empty receptacle thereof.

The material handler 18 may be carried by the housing 12 in any suitable manner for movement of medication out of the housing 12. For example, the material handler 18 may be supported by the material handler wall 42 and between the sidewalls 28 of the main body 20 so as to feed or convey the packaged medication strip 14 out of the housing 12 through the outlet 66. The material handler 18 may include a powertrain including a prime mover 114. The prime mover 114 may be an electrical motor or any other suitable device. The powertrain also may include a drivetrain coupled to the prime mover or motor 114 in any suitable manner. The drivetrain may include a transmission 115 having its input coupled to the motor 114 and drive elements 116 coupled to the output shaft 45 to drive the strip 14. The drive elements 116 may be toothed wheels or gears, or other meshing elements, or any other suitable drive elements. The material handler 18 also may include driven elements 118 on the driven shaft 47 on a side of the medication packaging strip 14 opposite that of the drive elements 116.

The medication packaging strip 14 may be rolled or folded back onto itself in a compact manner within the housing 12 as illustrated, or may be wound on a spool or reel, or the like. As used herein, the term medication may include anything for topical treatment or internal care of patients and in any form, including but not limited to solids, liquids, powders, gels, creams, lotions, ointments, syringes, sprays or sprayers, bandages, gauze, or any other supplies.

Referring to FIGS. 2 and 5, the strip 14 may include a base 120, and a cover 122 over at least a portion of the base 120. As best shown in FIG. 5, the strip 14 also may include a plurality of spaced apart tear lines 124 defining a plurality of individual packages 14a, 14b each of which may have a leading edge 126, a trailing edge 128, and side edges 130 extending between the front and trailing edges 126, 128. The tear lines 124 may be predefined by perforations, weakenings, thinnings, frangible connectors, or any other suitable features. Each individual package 14a, 14b also may have an upper surface 132 (FIG. 2), and a bottom surface 134. In one embodiment, the bottom surfaces 134 may be reflective surfaces with one or more sensor pickups 136. For example, the bottom surfaces 134 may be white for good reflectivity and the pickups 136 may be black for good contrast. Like the guide surfaces, the bottom surfaces 134 may be sufficiently smooth and bright to provide good reflection for sensor activation. In fact, the white guide surfaces and the white bottom surfaces 134 may be colored so as to mimic reflectivity of one another.

Each individual package 14a, 14b also may have a dose of medication 138 (FIG. 2) disposed between corresponding portions of the cover 122 and the base 120. As used herein, the term "dose" may include one or more individual tablets, capsules, or the like. The strip 14 may be released from the drawer 10 on a unit dose, unit-of-use, or dose-by-dose basis. For example, an operator may use any suitable input device to instruct the computer 520 to power the motor 114 to advance the leading individual package of the strip 14 in a downstream direction out of the outlet 66. As the strip 14 is advanced downstream, the sensors 86 sense the absence of the pickups 136 by way of the reflective guide surfaces 102 of the packaging strip guide 94, and then by way of the white surfaces of the packaging strip.

The motor 114 will continue to operate until the sensor pickups 136 on the leading package 14a of the strip 14 align with the sensors 86 wherein the sensors 86 sense the presence of the pickups 136. At this point, the computer receives signals (e.g. binary "1") from the sensors 86 and depowers the motor 114 in response thereto.

A suitable portion of the first package 14a projects beyond the front cover 26 to allow a user to grasp the package 14a, and pull and tear the package 14a away from the second package 14b. When the first package 14a has been removed, the sensors 86 sense the absence of the pickups 136 by way of the reflective surfaces 102 provided by the guide 94. At this point, the computer receives signals (e.g. binary "0") from the sensors 86 and maintains the motor 114 in a depowered state.

Again, a user may use a suitable input device to instruct the computer to power the motor 114 to advance the subsequent individual package of the strip 14 toward and out of the outlet 66. Again, the sensors 86 sense the absence of the pickups 136 by way of the reflective surfaces 102 provided by the guide 94 wherein the computer receives signals (e.g. binary "0") from the sensors 86 and maintains the motor 114 in a powered state. Therefore, the motor 114 will continue to operate until the sensor pickups 136 on the subsequent package 14b of the strip 14 align with the sensors 86 wherein the sensors 86 sense the presence of the pickups 136. At this point, the computer receives signals (e.g. binary "1") from the sensors 86 and depowers the motor 114 in response thereto.

As the computer powers the motor 114, the computer also powers the light 87 to indicate which drawer(s) of a plurality of drawers 10 in a medication cabinet are releasing medication. For example, the computer may power the light 87 in a steady or blinking manner to alert an operator as to which drawer should be releasing one or more packages of the strip 14.

In one embodiment, the sensors 86 may operate as part of a medication counter so that the quantity of medication doses that passes through the outlet 66 can be counted. For example, each time the leading individual package of the strip 14 is advanced through the outlet 66, the sensors 86 sense the pickups 136 and the computer 520 may receive a corresponding indication from the sensors 86 that may be used to increment any suitable counter in the computer 520 to track the quantity of individual packages that have been advanced or released. In another example, each time the leading individual package of the strip 14 is removed from the rest of the strip 14 through the outlet 66, the sensors 86 sense the absence of the pickups 136 and the computer may receive a corresponding indication from the sensors 86 that may be used to increment a counter in the computer 520 to track the quantity of individual packages that have been released.

Figure 6:
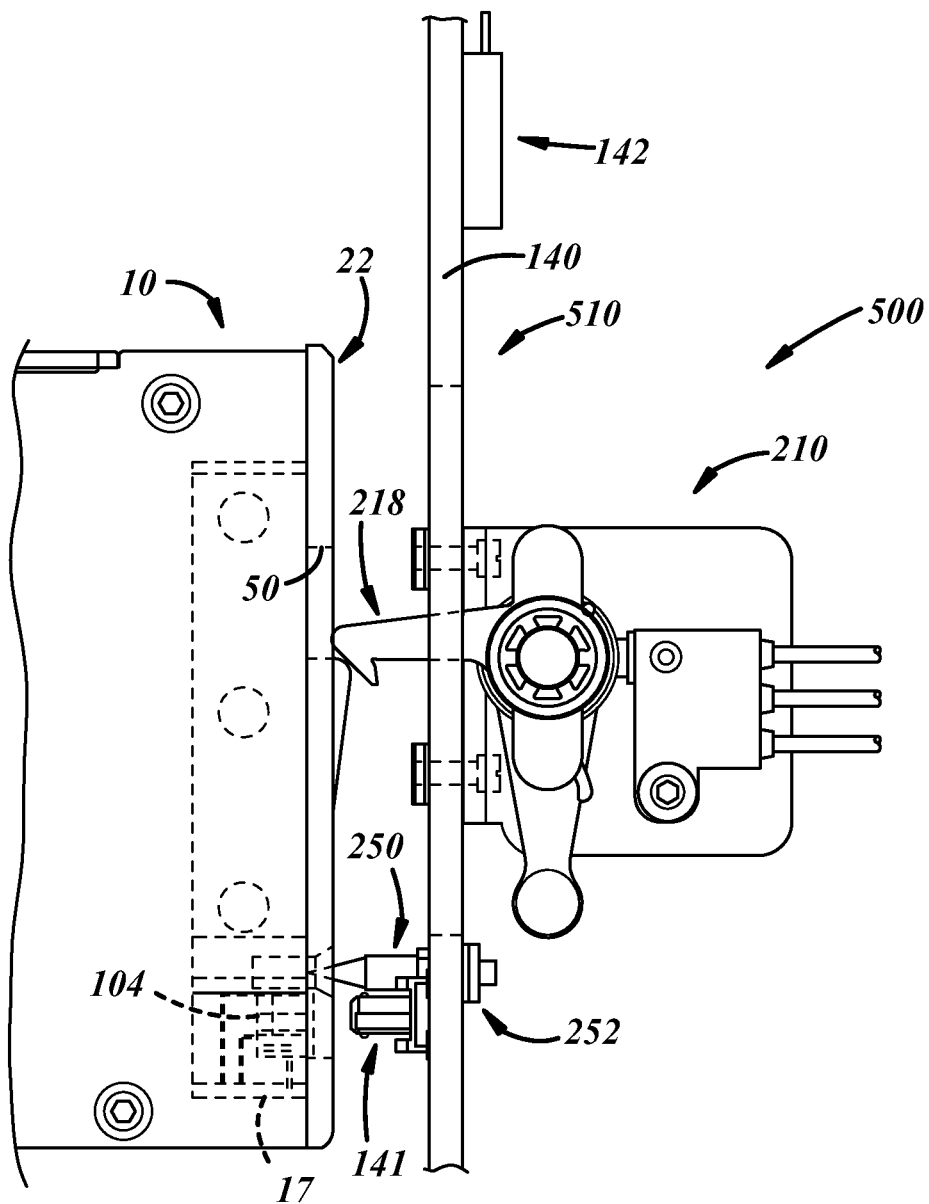
FIG. 6 is a fragmentary side view of a portion of the apparatus of FIG. 1, illustrating initial engagement of one of the drawers of FIG. 1 with a portion of the housing.

Referring now to FIG. 6, each drawer 10 may include the electrical connector 104 that may be coupled to and carried by the circuit board 17 in any suitable manner, for example, by soldered pins. Likewise, the apparatus 500 also may include an electrical connector 141 that may be coupled to a backplane 140 of the apparatus 500 in any suitable manner, for example, by soldered pins. The apparatus 500 may include a plurality of the connectors 141 corresponding to the plurality of receptacles. The backplane 140 may be carried by the housing 510, for instance, via internal framework and fasteners, or in any other suitable manner. The illustrated connector 141 may be the counterpart connector for the drawer connector 104. The connectors 104 and 141 are coupled to their respective supports such that they align and engage with one another. The connectors 104, 141 may be 10 pin connectors, and one or both may incorporate a floating insertion feature that allows a male end of the connector(s) to float horizontally and vertically making insertion easier. Of course, although not shown in the drawings, any suitable power and data wires or the like may be coupled between the latch and ejector 210 and connector 141 and corresponding portions of the apparatus 500, such as a power supply, controller, and/or the like. The connectors 104, 141 may be low friction connectors constructed so that the drawer connector 104 is inherently guided into the mating cart connector 141 with little to no effort, for example, 0.1 to 0.4 lbs of force and, more specifically about 0.2 lbs of force. Also, the low friction connectors 104, 141 are constructed so that the drawer connector 104 is easily disengaged from the mating cart connector 141 when the drawer 10 is unlatched from the housing of the apparatus 500.

The housing 510 also may carry a wireless transceiver 142 in communication with the computer to read data from and write data to the RFIC memory 106'. The transceiver 142 may include a wireless Generation 2 interrogator available from Ramtron or any other suitable source.

The backplane 140 may be communicated in any suitable manner to the computer 520, which may be in communication with the connectors 141 via the backplane 140 and may be programmed in accord with the array of receptacles 516. Accordingly, the locations of the drawers 10 in the receptacles 516 can be communicated to and stored in the computer 520 in any suitable manner.

The apparatus 500 also may include a guide pin 250 that may be coupled to the backplane 140 to align the drawer 10 with respect to the backplane 140 for good alignment of the connectors 104, 141 and the latch and ejector 210 with respect to the latch aperture 50. For example, the guide pin 250 may extend through the backplane 140 and a fastener 252 may fasten the guide pin 250 to the backplane 140. The guide pin 250 is adapted for cooperation with a corresponding guide pin passage of the drawer 10.

In use, the drawer 10 may be pushed toward the backplane 140 wherein a latch member 218 contacts a rear wall of the drawer 10, for example, the rear surface of the rear cover 107 of the drawer 10. Also, the guide pin 250 engages the guide pin passage, and the connectors 104, 141 eventually operatively engage one another.

The drawer 10 continues advancing, and reaches its closed position wherein the drawer 10 is fully inserted in its corresponding receptacle. At this point, the latch member 218 has been pivoted from its home position and a barb of a bayonet end of the latch member 218 has cleared a rear inside surface of the drawer 10 adjacent the aperture 50. Also, the latch member 218 has dropped or moved into a latched position with the bayonet engaged with the base wall 48 of the rear cover 22 of the drawer 10. The drawer 10 will remain in the latched state until a signal is sent from the computer 520 (FIG. 1) of the apparatus 500 to the actuator 214 to unlatch the drawer 10. Also, at this point, the connectors 104, 141 are operatively engaged and the computer 520 (FIG. 1) may recognize the drawer 10 using, for example, any suitable plug-and-play utility like USB, or the like. In other words, the connectors 104, 141 may be configured as part of a drawer presence detection device wherein the computer 520 recognizes that the drawer 10 is engaged to the apparatus 500 when the connection between the connectors 104, 141 is made.

Figure 7:
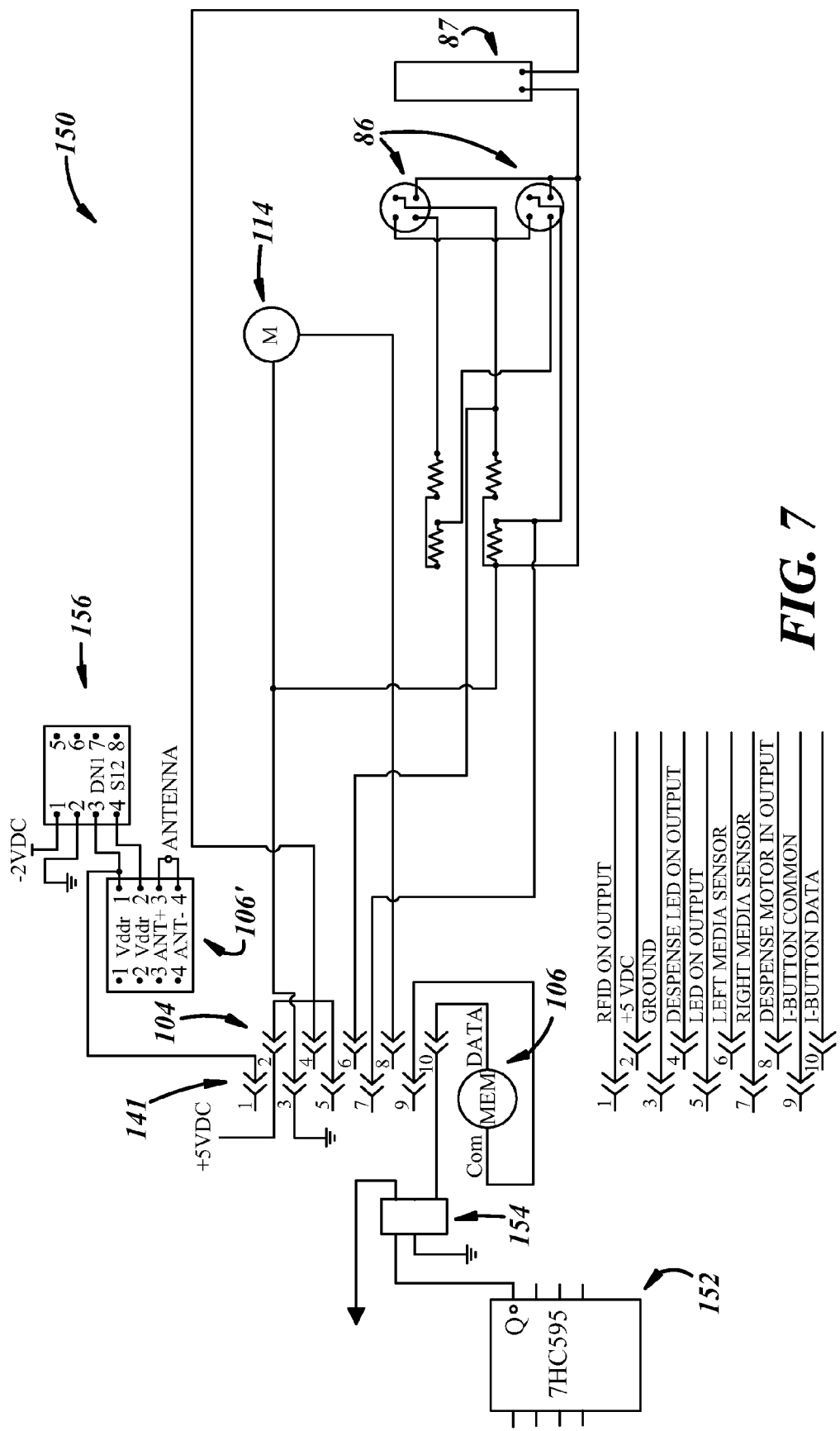
FIG. 7 is an electrical schematic of an illustrative embodiment of portions of the computerized medication administering apparatus of FIG. 1 including memory circuitry.

FIG. 7 illustrates circuitry 150 of the apparatus 500, wherein the drawer connector 104 is adapted to be coupled to the apparatus connector 141 of the apparatus 500. The circuitry 150 also may include the connectors 104, 141, which may be configured as a part of a cassette presence detection device wherein the computer 520 recognizes that the drawer 10 is engaged to the cart 510 of the apparatus 500 when the connection between the connectors 104, 141 is made. This may replace or supplement functionality of a cassette or drawer presence switch (not shown), which may be powered by the cart 510 and communicated to the computer 520, and arranged so as to sense the operative engagement of the drawer 10 with the cart 510. The circuitry 150 may include the motor 114 including ground and power connections, the light 87 including ground and power connections, and the sensors 86 including suitable interconnections, power connections, motor ground connections, and corresponding pull down resistors.

The circuitry 150 also may include the memory 106 carried by the drawer 10, and a digital chip 152 and a relay 154 that may be carried by the cart 510, for instance, on the backplane. The relay 154 has a memory data input pin coupled to a memory data output of the memory 106 via the connector 104, and a memory data output pin coupled to the computer 520 in any suitable manner for communication of memory data to the computer 520. The digital chip 152 and/or memory 106 may be coupled to the computer 520 in any suitable manner, for example, via one or more input/output controllers (not shown). The relay 154 also has a ground pin coupled to ground in any suitable manner, and control input pin coupled to a control output pin of the chip 152. The memory 106 has a common lead coupled to common pins of the connectors 104, 141. The chip 152 may include any suitable serial data chip, for instance, an NXP brand shift register with latches, model 74HC595 available from NXP Semiconductors of Eindhoven, Netherlands. The relay 154 may be a solid state, optically coupled, MOSFET relay, model CPC1008N available from Clare/Ixys of Beverly, Mass. The circuitry 150 may be provided with power by the power supply 518 in any suitable manner.

The circuitry 150 further may include the RFIC memory 106' carried by the drawer 10, and a metal oxide semiconductor field-effect transistor (MOSFET) 156 coupled to the RFIC memory 106'. The MOSFET 156 may include a matched pair MOSFET array, for instance, a model ALD110900A available from Advanced Linear Devices of Sunnyvale, Calif. The MOSFET 156 includes a ground pin coupled to ground in any suitable manner, a power input pin coupled to any suitable power source, for example, the power supply 518 and in any suitable manner, a drain pin coupled to a power supply input pin of the memory 106', and a source pin coupled to an RF field power supply output pin of the memory 106'.

Ordinarily, the RFIC memory 106' may be triggered to communicate wirelessly with the transceiver 142 by receiving a wireless interrogation signal. The RFIC memory 106' includes an antenna and corresponding antenna pins, a voltage input pin to receive a voltage signal that causes the RFIC memory 106 to communicate wirelessly with the transceiver 142, and a voltage output pin that normally communicates internally generated voltage to the voltage input pin when interrogated by the transceiver 142. As used herein, the term "trigger" means to initiate, actuate, or set off memory to read out or be written to.

The MOSFET 156 is constructed such that a normally closed switch is effectively defined between the drain and source pins, wherein the switch is opened when the MOSFET power input pin receives suitable power, for instance 0.2 Volts, when the drawer and housing electrical connectors 104, 141 are operatively engaged. The drain and source pins are coupled across the voltage output and input pins of the RFIC memory 106'. Accordingly, when the MOSFET is powered, the voltage output and input pins of the RFIC memory 106' are decoupled such that the RFIC memory 106' cannot be activated to communicate wirelessly with the transceiver 142, unless voltage is separately applied to the voltage input pin of the RFIC memory 106'. Therefore, the voltage input pin of the RFIC memory 106' is coupled to the connectors 104, 141 to receive a voltage input that may be controlled by the computer 520 in any suitable manner. But when the drawer 10 is not operatively engaged with the housing 510, no power is applied to the MOSFET and, thus, the RFIC memory 106' may be interrogated without having to apply an external voltage to the voltage input pin of the RFIC memory 106'. Accordingly, the voltage input to the voltage input pin of the RFIC memory 106' triggers the memory 106' to transmit data to the computer 520.

Accordingly, the apparatus 500 includes a means for selectively communicating data to and/or from non-volatile read/write memory of the plurality of the drawers. More specifically, the apparatus 500 may include a means for selectively transmitting data from among non-volatile read/write memory of the plurality of the drawers. For example, in one embodiment, the means may include the memory 106, the digital chip 152, and the relay 154. In another embodiment, the means may include the RFIC memory 106', and the metal oxide semiconductor field-effect transistor (MOSFET) 156 coupled to the RFIC memory 106'. In either or both embodiments, the means may also include the computer 520 (or output signals therefrom), any suitable power supply and wireless or wired connections. In other embodiments, the means may include any suitable hardware, software, and/or firmware to cause non-volatile read/write memory carried by the drawer 10 to selectively transmit and/or receive data to and/or from the computer 520. As used herein, the term "selective" includes selection of one of a group.

In operation, once the drawer 10 is inserted into the housing 510 of the apparatus 500 such that the connectors 104, 141 are operatively engaged, the computer 520 recognizes that the drawer 10 is present. For example, a USB plug and play utility can be executed on the computer 520 wherein an input corresponding to the receptacle is set to a logical "1" indicating presence of the drawer 10 in a corresponding receptacle.

Thereafter, in one embodiment, the computer 520 activates the data relay 154 in any suitable manner, for instance, by outputting a signal thereto via the digital chip 152. Accordingly, activation of the data relay 154 triggers the memory 106 to transmit data stored in the memory 106 back to the computer 520. In another embodiment, the computer 520 activates the RFIC memory 106' in any suitable manner, for example, by outputting a voltage signal to the voltage input pin thereof via the connectors 104, 141 in any suitable manner.

In either embodiment, the computer 520 reads the data output from the memory 106 and/or 106' and stores the data in memory of the computer 520, for instance, in an eMAR database. Once the data is read by and/or stored in computer memory, the computer 520 deactivates the data relay 154 or the RFIC memory 106'. Thereafter, the computer 520 may upload the data from the apparatus 500 to a network as will be described below. The previously read and stored data can be confirmed, for example, by comparing drawer data in the computer database with corresponding data for that drawer on the network, for instance, from a pharmacy network database. In one example, the medication count in a drawer and the drawer serial number can be confirmed. Because the memory 106 and/or 106' is serialized, the computer 520 can recognize the drawer 10 regardless of which receptacle 516 receives the drawer 10.

In one embodiment, after initial full operative engagement of the drawer 10 with a corresponding receptacle 516, an operator may request release of one or more packets of medication from the drawer 10, for example, via the user interface 514. In response, the computer 520 may transmit a signal to activate the medication conveyor to move one or more packets out of the drawer 10. Thereafter, the operator may remove the packet(s) by tearing the packet(s) from the medication strip as discussed previously. Accordingly, the sensor(s) 86 will sense conveyance of the medication packet(s) through the outlet of the drawer 10, and a medication count for the drawer 10 may be correspondingly decremented in memory of the computer 520. Accordingly, the computer 106 receives data only from the memory 106 of the drawer 10 from which the medication was conveyed or administered. Later, the operator may request release or ejection of the drawer 10 from the housing 510, for example, via the user interface 514. But before the computer 520 outputs an appropriate signal to the latch and ejector 210, the computer 520 may transmit the drawer data from computer memory to the drawer memory 106. Accordingly, after the drawer 10 is operatively engaged to the cart 510, the drawer memory 106 may be updated after the operator requests removal of the drawer 10 from the cart 510.

In another embodiment, the computer 520 may selectively read the memory 106 and/or 106' from the drawer 10 after the drawer 10 is operatively engaged to the cart 510 and the operator requests release of medication from the drawer 10 via the user interface 514. In response, the medication conveyor moves the dose(s) out of the drawer 10, and the operator removes the dose(s). Accordingly, the sensor(s) 86 will sense removal of the medication dose(s) from the drawer 10, and a medication count for the drawer 10 is correspondingly decremented in the drawer memory 106. At that point, the computer 520 may activate the data relay 154 to trigger the memory 106 to transmit data stored in the memory 106 to the computer 106, which reads, confirms, saves, and uploads the data. Accordingly, the computer 106 receives data only from the memory 106 of the drawer 10 from which the medication was dispensed. Therefore, there is no need to poll all of the drawers every time medication is released from one of the drawers of the apparatus and, thus, data from one drawer will not become confused with data from another drawer in the computer database.

Figure 8:
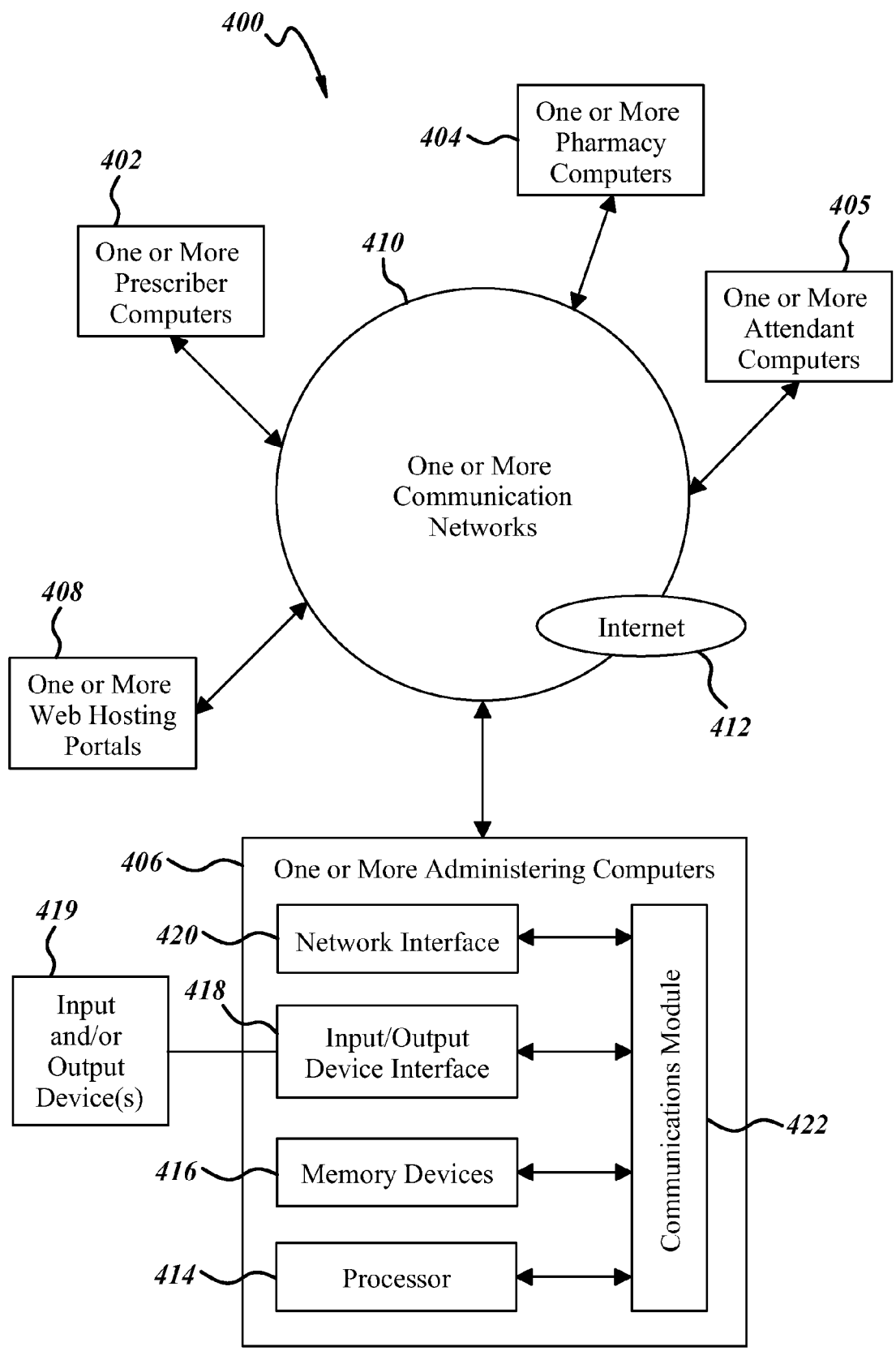
FIG. 8 is a block diagram illustrating a computing system according to one exemplary embodiment.

FIG. 8 shows one example of a system 400 to implement method and/or apparatus aspects of the present disclosure. The system 400 may include one or more of the following subsystems, or system elements or components: one or more physician or prescriber computers 402 for receiving, processing, and transmitting data; one or more pharmacy computers 404 for receiving, processing, and transmitting data; one or more nurse or attendant computers 405 for receiving, processing, and transmitting data; one or more administering computers 406, which may include the aforementioned apparatus computer 520, for receiving, processing, and transmitting data; one or more web-hosting servers 408 that may host one or more websites or network portals; and one or more communication networks 410, which may include a wide area network (WAN), for example the Internet 412, for providing communication among the various system elements. Those of ordinary skill in the art will recognize that the various computers 402, 404, 406, 408 may have hardware and software aspects in common, which will not be repeated for each computer description. Accordingly the descriptions of the various computers are mutually incorporated by reference.

Although the system 400 may include computers, for purposes of this disclosure, the system 400 may include any instrumentality or aggregation of instrumentalities operable to compute, classify, detect, display, handle, originate, manipulate, manifest, process, record, reproduce, receive, retrieve, switch, store, or utilize any form of data, information, intelligence for academic, business, production, scientific, or other purposes. Although described in connection with an exemplary computing system environment, the disclosed methods may be operational with numerous other special purpose computing system environments or configurations. The computing system environment is not intended to suggest any limitation as to the scope of use or functionality of the system or method.

Moreover, the computing system environment should not be interpreted as having any dependency or requirement relating to any one component, or combination of components, illustrated in the exemplary operating environment. Examples of well known computing systems, environments, and/or configurations that may be suitable for use include, but are not limited to, personal computers, server computers, hand-held or laptop devices, multiprocessor systems, microprocessor-based systems, set top boxes, programmable consumer electronics, personal digital assistants, mobile telephones, network PCs, minicomputers, mainframe computers, distributed computing environments that include any of the above systems or devices, and/or the like.

In general, the administering computer 406 may receive input from the various devices of the administering apparatus 500 and/or other computers 402, 404, 408, at least partially enable or carry out method steps disclosed herein, and transmit output to the various devices of the administering apparatus 500 and/or the various other computers 402, 404, 408. To facilitate such functionality, the administering computer 406 may have a processor 414, one or more memory 416 in communication with the processor 414 such as an internal memory and/or an external memory, an input/output device interface 418, a network interface 420, and a communications module 422.

The communications module 422 may be any type of suitable module including a system bus, which may couple one or more of the various above-described system components or modules. The system bus may provide for data transmission internally between the elements in the computer and externally between the internal elements of the computer 406 and any other elements external of the computer 406.

The processor 414 may be configured to execute instructions or control logic that provides at least some functionality of the disclosed methods. In this respect, the processor 414 may encompass one or more processing units, controllers, microprocessors, micro-controllers, discrete logic circuit(s) having logic gates for implementing logic functions upon data signals, application specific integrated circuits (ASIC) with suitable logic gates, complex programmable logic devices (CPLD), programmable or field-programmable gate arrays (PGA/FPGA), any combinations of the aforementioned, and the like. As used herein, the term processor may also include any ancillary devices such as clocks, power supplies, and the like.

The memory 416 may include computer readable storage or media in the form of removable and/or non-removable, volatile memory and/or non-volatile memory. Exemplary volatile memory may include random access memory (RAM), static RAM (SRAM), dynamic RAM (DRAM), and the like, for running software and data on the processor. Exemplary non-volatile memory may include read only memory (ROM), erasable programmable ROM (EPROM), electrically erasable programmable ROM (EEPROM), dynamic read/write memory like magnetic or optical disks or tapes, and static read/write memory like flash memory, for storing software and data.

The input/output device interface 418 may be used to communicate the administering computer 406 with user selection devices or one or more input peripheral devices 419. Such devices may include a pointing device (e.g., a mouse, trackball, pen, touch pad, touchscreen, or the like), keyboard, modem, internal card reader, and the like, that may be used to enter commands and data into the computer 406. Other input devices (not shown) may include a microphone, joystick, satellite dish, wireless communication device, proximity sensor, scanner, or the like. The input/output interface 418 may connect the above described input devices, and possibly other input devices, to the processor 414 via the system bus 422, but may connect via other interfaces and bus structures, such as a parallel port, Universal Serial Bus (USB), infrared device, or the like.

The input/output device interface 418 may be used to communicate the administering computer 406 with one or more output peripheral devices (not shown). The output peripheral devices may include a printer, a monitor, or other type of display device or other peripheral device such as speakers (not shown), and the like, and also may be connected to the system bus 422 via the input/output interface, which may be any suitable printer, video, etc., type of interface. One example of a combined input/output peripheral device includes the touch screen monitor 14 of the administering apparatus 500.

The network interface 420 may include any suitable communication device such as a wired or wireless telephone device, dial-up modem, cable modem, or the like for communicating the computer 406 with the communications network 410. The network interface 420 may enable transmission and reception of voice, data, fax, and/or like transmissions to and from the network 410.

As used herein, the term interface broadly means any suitable form of electronic device or adapter, or even a software module or adapter, which enables one piece of equipment to communicate with or control another. Any of the interfaces disclosed herein may conform to any suitable protocols such as Ethernet or field buses such as Profibus, Interbus, Devicenet, RS-232, parallel, small computer interface, USB, wireless protocols such as Bluetooth, infrared, and the like, and any other suitable input/output (I/O) protocols.

As shown, the computer 406 may operate in a networked environment, in communication with one or more remote computers, which may include the prescriber and/or pharmacy computers 402, 404. In any case, the remote computers may be personal computers, servers, routers, network PC's, peer devices, other common network nodes, and the like. In a networked environment, software and/or data used by the computer, or portions thereof, may be stored in the remote computer or a remote memory storage device (not shown) associated therewith or connected thereto. By way of example, and not limitation, remote application programs/data may reside in memory of the remote computer(s).

At least some portion of the disclosed methods may be practiced locally or in a distributed computing environment where tasks may be performed by the various computers 402, 404, 406, 408 that are linked through the communications network 410. In a distributed computing environment, programs may be located in both local and remote computer storage media including memory storage devices. It is therefore to be understood that the presently disclosed methods may be at least partially performed by any computing devices suitable for executing one or more of the specified functions, using any media and being located anywhere.

Computer programs or software may include executable instructions for implementing logical functions and can be embodied in any computer-readable medium for use by or in connection with the processor 414, which may retrieve and execute the instructions. The software may include, but is not limited to routines, modules, objects, components, data structures, and the like, for performing particular tasks and/or implementing particular abstract data types. General examples include software programs comprised of instructions in source code, object code, executable code or other formats; firmware programs; or hardware description language (HDL) files; and the like. Specific examples include assembler, C, C++ objects, C# sharp, object oriented programming, Visual Basic, Visual C++, XML, Java, and Microsoft® (MS) Foundation Classes, Microsoft.net, visual.net, PERL, PHP, SQL, and/or the like.

In general, the communication network 410 may be any suitable local area network, wide area network including the Internet 412, or the like. The communication network 410 may include a wireless system, land network, any combination thereof, or the like, that is adapted to transmit and receive signals to and from one or more of the prescriber computers 402, pharmacy computers 404, administering computers 406, and or web hosting server 408.

In one specific implementation, the communication network 410 may include a wireless carrier system including a wireless communications carrier, a mobile telephone system, satellite broadcast system, or the like, that may incorporate any type of telecommunications in which electromagnetic waves carry signals over part of or an entire communication path. For example, the wireless carrier system may be implemented as a CDMA, GSM, or other cellular communication system, or any other suitable wireless system.

In another specific implementation, the communication network 410 may also or instead include a land network used to connect the computers 402, 404, 406, and web-hosting server 408. As such, the land network may be a public-switched telephone network (PSTN), an Internet protocol (IP) network, wired network, optical network, fiber network, and/or any combination thereof. The land network may be connected to one or more landline telephones, facsimile machines, computers, or the like.

The network 410 may include a local area network (LAN) and/or a wide area network (WAN), but may also include any other suitable networks, connections, and/or protocols. The LAN and/or WAN may be a wired network, a wireless network, a combination thereof, and the like. When used in a local area networking environment, the computer is preferably connected to the LAN through the network adapter or interface 420. When used in a wide area networking environment, the computer preferably includes the modem or any other means for establishing communications over the WAN. The modem, which may be internal or external, is preferably connected to the system bus via the input interface, or other appropriate arrangement. The network connections shown are exemplary and other means of establishing a communications link between the computers 402, 404, 406 may be used.

The web-hosting server 408 may include one or more communication devices for communicating with the communication network 410, and one or more server computers. The web-hosting server 408 may be directly connected by phone lines, cable lines, fiber optic cable, and/or wirelessly to any suitable land network or wireless network, for example, via the communications network 410. The web server computer may be implemented as any suitable hardware and software capable of providing Internet services to receive and transmit data from and to the computers 402, 404, 406. In an exemplary implementation, the web server 408 may include a computer for executing and storing computer applications, data files or records, and/or databases for managing and storing data supplied by the computers 402, 404, 406.

As used in the sections above and claims below, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components, elements, or items. Similarly, when introducing elements of the invention or the example embodiments thereof, the articles "a," "an," "the," and "said" are intended to mean that there are one or more of the elements. Moreover, directional words such as front, rear, top, bottom, upper, lower, radial, circumferential, axial, lateral, longitudinal, vertical, horizontal, transverse, and/or the like are employed by way of description and not limitation. Other terms are to be construed using their broadest reasonable meaning unless they are used in a context that requires a different interpretation.

Finally, the foregoing description is not a definition of the invention, but is a description of one or more examples of exemplary embodiments of the invention. The statements contained in the foregoing description relate to the particular examples and are not to be construed as limitations on the scope of the invention as claimed below or on the definition of terminology used in the claims, except where terminology is expressly defined above. And although the present invention has been disclosed using a limited number of examples, many other examples are possible and it is not intended herein to mention all of the possible manifestations of the invention. In fact, other modifications, variations, forms, ramifications, substitutions, and/or equivalents will become apparent to those skilled in the art in view of the foregoing description. The present invention is intended to embrace such forms, ramifications, modifications, variations, substitutions, and/or equivalents as fall within the spirit and broad scope of the following claims. In other words, the present invention encompasses many substitutions or equivalents of limitations recited in the following claims. For example, the materials, sizes, and shapes, described above could be readily modified or substituted with other similar materials, sizes, shapes, and/or the like. Therefore, the invention is not limited to the particular examples of exemplary embodiments disclosed herein, but instead is defined solely by the claims below.

What is claimed is:

1. A medication administering apparatus, comprising:
   a housing including a plurality of receptacles and a plurality of housing electrical connectors corresponding to the plurality of receptacles;
   a plurality of medication drawers corresponding to the plurality of receptacles, wherein a drawer of the plurality of drawers carries:
      a drawer electrical connector to couple to one of the housing electrical connectors when the drawer is inserted in a receptacle of the plurality of receptacles;
      a medication conveyor; and
      a non-volatile read/write memory to store data about the drawer;
   a computer in communication with the plurality of housing electrical connectors; and
   a means for selectively transmitting data from among the non-volatile read/write memory of the plurality of medication drawers, wherein when a medication drawer of the plurality of medication drawers is inserted into a corresponding receptacle such that corresponding drawer and housing electrical connectors are operatively engaged, the selectively transmitting data means triggers the memory of the inserted drawer to transmit data stored therein to the computer.

2. The medication administering apparatus of claim 1, wherein the computer recognizes the drawer regardless of which one of the plurality of receptacles receives the drawer.

3. The medication administering apparatus of claim 1, wherein when medication is dispensed from the drawer by activation of the medication conveyor by the computer, a medication count for the drawer is decremented in the memory, and the computer activates the selectively transmitting data means to trigger the memory to transmit data to the computer, such that the computer receives data only from the memory of the drawer from which the medication was dispensed.

4. The medication administering apparatus of claim 1, wherein each of the plurality of drawers also includes a circuit board assembly including a circuit board carrying the memory.

5. The medication administering apparatus of claim 1, wherein the memory is in wired communication with the computer via the electrical connectors.

6. The medication administering apparatus of claim 1, wherein the housing also carries a wireless transceiver in communication with the computer, and wherein the memory communicates with the computer via the wireless transceiver.

7. The medication administering apparatus of claim 1, wherein the read/write memory includes wired memory and the selectively transmitting data means includes a data relay coupled to the wired memory and the drawer electrical connector.

8. The medication administering apparatus of claim 1, wherein the read/write memory includes wireless RFIC memory and the selectively transmitting data means includes a normally closed switch that is coupled across voltage output and input pins of the RFIC memory and that is powered to be open when the drawer and housing electrical connectors are operatively engaged.

9. The medication administering apparatus of claim 1, wherein the read/write memory includes wireless RFIC memory and the selectively transmitting data means includes a MOSFET coupled to the RFIC memory to prevent the RFIC memory from being interrogated until the computer outputs an activation signal to the RFIC memory.

10. The medication administering apparatus of claim 1, wherein the computer receives data only from the memory of the drawer that is inserted and not all of the drawers.

11. The medication administering apparatus of claim 10, further comprising:
   a wireless RFIC memory to store data about the drawer; and
   a MOSFET coupled to the RFIC memory to prevent the RFIC memory from being interrogated until the computer outputs an activation signal to the RFIC memory, wherein when the drawer is inserted into the receptacle such that the drawer and housing electrical connectors are operatively engaged, the computer outputs a signal to the RFIC memory to trigger the memory to transmit data stored therein to the computer.

12. A medication administering apparatus, comprising:
   a housing including a plurality of receptacles and a plurality of housing electrical connectors corresponding to the plurality of receptacles;
   a plurality of medication drawers corresponding to the plurality of receptacles, wherein a drawer of the plurality of drawers carries:
      a drawer electrical connector to couple to one of the housing electrical connectors when the drawer is inserted in a receptacle of the plurality of receptacles;
      a medication conveyor; and
      a read/write memory to store data about the drawer;
   a computer in communication with the plurality of housing electrical connectors; and
   a data relay coupled between the computer and the drawer memory, wherein when the drawer is inserted into the receptacle such that the drawer and housing electrical connectors are operatively engaged, the computer outputs a signal to the data relay to trigger the memory to transmit data stored therein to the computer.

13. The medication administering apparatus of claim 12, wherein when medication is dispensed from the drawer by activation of the medication conveyor by the computer, a medication count for the drawer is decremented in the memory, and the computer activates the data relay to selectively trigger the memory to transmit data to the computer, such that the computer receives data only from the memory of the drawer from which the medication was dispensed.

14. A medication administering apparatus, comprising:
a housing including a plurality of receptacles and a plurality of housing electrical connectors corresponding to the plurality of receptacles;
a plurality of medication drawers corresponding to the plurality of receptacles, wherein a drawer of the plurality of drawers carries:
   a drawer electrical connector to couple to one of the housing electrical connectors when the drawer is inserted in a receptacle of the plurality of receptacles;
   a medication conveyor; and
   a wireless read/write RFIC memory to store data about the drawer;
a computer in communication with the plurality of housing electrical connectors; and
a MOSFET coupled to the RFIC memory to prevent the RFIC memory from being interrogated until the computer outputs an activation signal to the RFIC memory, wherein when the drawer is inserted into the receptacle such that the drawer and housing electrical connectors are operatively engaged, the computer outputs a signal to the RFIC memory to trigger the memory to transmit data stored therein to the computer.

15. The medication administering apparatus of claim 14, wherein when medication is dispensed from the drawer by activation of the medication conveyor by the computer, a medication count for the drawer is decremented in the memory, and the computer activates the MOSFET to selectively trigger the RFIC memory to transmit data to the computer, such that the computer receives data only from the RFIC memory of the drawer from which the medication was dispensed.

16. A method of administering medication, comprising:
storing medication in a plurality of drawers wherein each of the plurality of drawers includes a drawer electrical connector, a medication conveyor, and a non-volatile read/write memory to store data about the drawer;
inserting a drawer of the plurality of drawers into a receptacle of a housing, wherein the receptacle is one of a plurality of receptacles, and the housing also includes a plurality of housing electrical connectors corresponding to the plurality of receptacles, wherein one of the housing electrical connectors is coupled to the electrical connector of the drawer when the drawer is inserted in the receptacle; and
selectively transmitting data from among non-volatile read/write memory of the plurality of drawers to a computer in communication with the plurality of housing electrical connectors, wherein when the drawer is inserted into the receptacle such that the drawer and housing electrical connectors are operatively engaged, the memory of the inserted drawer is triggered to transmit data stored therein to the computer.

17. The method of claim 16, wherein when the drawer is inserted into the receptacle such that the drawer and housing electrical connectors are operatively engaged, the memory of the inserted drawer is triggered using at least one of a relay or a switch to transmit data stored therein to the computer.

18. The method of claim 17, further comprising:
dispensing medication from the drawer, wherein dispensing include activating the medication conveyor via the computer;
decrementing a medication count for the drawer in the memory; and
activating at the computer the at least one of the relay or the switch to selectively trigger the memory to transmit data to the computer; and
in response to the activation, receiving data at the computer only from the memory of the drawer from which the medication was dispensed.

* * * * *